(12) United States Patent
Rosenfeldt et al.

(10) Patent No.: US 10,590,825 B2
(45) Date of Patent: Mar. 17, 2020

(54) LINE CONNECTOR WITH INTEGRATED SENSOR FOR MEASUREMENT OF UREA SOLUTIONS

(71) Applicant: VOSS AUTOMOTIVE GMBH, Wipperfürth (DE)

(72) Inventors: Sascha Rosenfeldt, Wipperfürth (DE); Christian Zwillus, Bergneustadt (DE); Waldemar Wilms, Marienheide (DE); Steve Inniger, Hoagland, IN (US)

(73) Assignee: VOSS Automotive GmbH, Wipperfurth (DE)

( * ) Notice: Subject to any disclaimer, the term of this patent is extended or adjusted under 35 U.S.C. 154(b) by 0 days.

(21) Appl. No.: 16/201,127

(22) Filed: Nov. 27, 2018

(65) Prior Publication Data

US 2019/0170045 A1 Jun. 6, 2019

Related U.S. Application Data

(63) Continuation-in-part of application No. 15/822,518, filed on Nov. 27, 2017.

(30) Foreign Application Priority Data

Nov. 26, 2018 (EP) .................................... 18208326

(51) Int. Cl.
*F01N 3/28* (2006.01)
*G01N 21/55* (2014.01)
(Continued)

(52) U.S. Cl.
CPC ......... *F01N 3/2896* (2013.01); *F01N 3/2066* (2013.01); *F16L 21/00* (2013.01);
(Continued)

(58) Field of Classification Search
CPC .. F01N 3/2066; F01N 3/2896; F01N 2610/02; F01N 2610/10; F01N 2610/14;
(Continued)

(56) References Cited

U.S. PATENT DOCUMENTS

| 9,388,932 B2 | 7/2016 | Ristovski et al. |
| 2014/0226149 A1* | 8/2014 | Coates .................. G01F 23/292 356/51 |
| 2019/0162093 A1* | 5/2019 | Rosenfeldt .............. F01N 3/208 |

FOREIGN PATENT DOCUMENTS

EP       2137449 B1    6/2011

* cited by examiner

*Primary Examiner* — Brandon D Lee
(74) *Attorney, Agent, or Firm* — Eric J. Sosenko; Jonathan P. O'Brien; Honigman LLP (57) ABSTRACT

A line connector for a fluid and a ready-made medial line including the line connector. The line connector includes a connecting piece with a flow-through channel in the interior thereof and extending in a longitudinal direction of the connecting piece. The connecting piece has at each of its two ends a coupling section that is designed such that a flexible media line or a tubing or an aggregate can be connected to an aggregate connector. The flow-through channel is provided with an electrical heating unit. In the region of the flow-through channel, between the connecting sections, a circumferential enclosed receiving housing is formed on the coupling piece and in which an optical sensor unit is disposed for measuring characteristics of the fluid flowing in the flow-through channel. The ready-made media line includes the line connector and a tubular media line connected on one or both ends thereof.

23 Claims, 6 Drawing Sheets

(51) Int. Cl.
*F16L 21/00* (2006.01)
*G01N 21/01* (2006.01)
*F16L 53/30* (2018.01)
*F01N 3/20* (2006.01)
*F16L 53/38* (2018.01)

(52) U.S. Cl.
CPC ............... *F16L 53/30* (2018.01); *F16L 53/38* (2018.01); *G01N 21/01* (2013.01); *G01N 21/55* (2013.01); *F01N 2610/02* (2013.01); *F01N 2610/10* (2013.01); *F01N 2610/14* (2013.01); *F01N 2610/148* (2013.01); *F01N 2900/1818* (2013.01)

(58) Field of Classification Search
CPC ........ F01N 2610/148; F01N 2900/1818; F16L 21/00; F16L 53/30; F16L 53/38; G01N 21/01; G01N 21/55
See application file for complete search history.

LINE CONNECTOR WITH INTEGRATED SENSOR FOR MEASUREMENT OF UREA SOLUTIONS

CROSS REFERENCE TO RELATED APPLICATION

This application is a continuation-in-part of U.S. application Ser. No. 15/822,518, filed Nov. 27, 2017, the entire contents of which are herein incorporated by reference.

BACKGROUND

1. Field of the Invention

The present invention relates to a line connector, comprising a connecting piece with a flow-through channel for a urea fluid in the interior thereof and extending in the longitudinal direction of the connecting piece, wherein the connecting piece comprises at each of its two ends a coupling section which is designed such that a flexible media line or a tubing or an aggregate to an aggregate connector can be connected, and the flow-through channel is provided with an electrical heating unit.

2. Related Technology

A line connector of this kind is known, for example, from EP 2 137 449 B1.

According to existing emissions requirements, a device known as an SCR-system is usually required for treatment of exhaust from diesel vehicles. In this regard, toxic nitrogen oxides are converted into harmless nitrogen and oxygen by the injection of a urea fluid in the region of an SCR catalyst.

The medium, the urea fluid, is drawn from a separate tank via lines and connectors to a dosing unit for injection of the urea fluid into the exhaust system. The quality and the proper mixing ratio of the urea fluid are monitored to satisfy the particular legal requirements. This is assured by a urea quality sensor.

The quality sensor today usually is seated in a tank to hold the urea fluid. It is either immersed in the medium there, or is seated in the tank wall. Immersed sensors are secured to a tank header unit (header unit) which also effects a thawing of the urea fluid in the tank. Sensors seated in the tank wall are secured in place by means of a device at the tank. A suitable gasket prevents the leakage of urea fluid out of the tank.

Various methods are known for electronically measuring the quality of the urea fluid. One known technique, for example, is the measurement of ultrasound wave transit times by means of an ultrasonic sensor. In addition, thermal or optical sensor systems are used.

Especially in commercial vehicles or off-road vehicles, the known measuring systems have the disadvantage that there are numerous, different tank geometries for the tank to hold the urea fluids, wherein for each tank the position of the sensor in or on the tank has to be determined anew. This produces a greater number of variants.

Pollutants appear in the tank holding the urea fluid, especially in commercial and off-road vehicles; these pollutants can move through the tank opening into the tank and can adversely affect the measurement of the quality of the urea fluid.

In addition, during fueling, a large number of air bubbles can be carried into the tank. Small bubbles can settle and/or adhere to the surface of the sensor. These bubbles in the urea fluid or on the surface of the sensor adversely impact the specific measurement.

Since the tank contains a not inconsiderable quantity of urea fluid at temperatures below the freezing point, larger chunks of ice can form within the tank fluid, which likewise negatively affect the measurement and can also damage the sensors by mechanically sloshing back and forth in the fluid.

Measurement sensors seated in the tank wall can result in the loss of a large volume of urea fluids, if they experience a leak. Furthermore, measurement sensors immersed in the tank are fully surrounded by the urea fluid. Thus all electrical connections also have to be introduced into the tank housing. In addition, they must be protected against penetration of the urea fluid. Any penetration of the urea fluid can result in destruction of the particular measurement sensor. Furthermore, the urea fluid can also creep into the cable harness of the connected electrical cables and cause additional destruction in the vehicle.

In case of needed service to replace the measurement sensor, the entire tank will have to be drained of the urea fluid, if the measurement sensors are seated in the tank wall. In the case of measurement sensors seated in the tank header, it will have to be fully disassembled, which is associated with significant effort and expense.

SUMMARY

The object of the present invention is to design an installation possibility for a measurement sensor to measure characteristics of the urea fluid, which avoids the above disadvantages and is distinguished by a compact and low-cost assembly.

This problem is solved by means of a line connector with the features of claim 1. The invention is based on the knowledge that the measurement of the characteristics of the urea fluid flowing in the flow-through channel takes place directly in the flow-through channel itself, so that thus the measurement sensor is itself a constituent of the line connector. Thus the installation of the measurement sensor is independent of the particular tank geometry; likewise the tank geometry can be selected independently of the installation of this kind of measurement sensor. Due to the integration of the measurement sensor into the line connector pollutants, which may be present in the tank, are no longer relevant to the measurement, because such pollutants generally are kept away from the line system itself by a filter. In addition, the problem of air bubbles adversely affecting the measurement result is avoided, even though these air bubbles are introduced during filling of the tank, they are not present in the line system, since it is difficult for air bubbles to settle permanently onto the surface of the sensor during the flow of the media during operation. Also, any ice chunks possibly present in a tank cannot affect the line system itself. If a leak occurs, any leakage of a large volume of the urea fluid need not be feared, since only a small amount of urea fluid is ever present in the line system itself. Accordingly, any leaking urea fluid cannot cause significant damage. Likewise, any leakage cannot result in significant destruction of other components of the vehicle, since the electrical connections are not immersed in the urea fluid itself. If service is needed, the particular line or sensor can be easily replaced together with or separate from the line connector. In addition, the sensor is easier to reach, and no additional precaution is needed, such as drainage of the tank, for example.

According to the invention, it is an advantage that in the region of the flow-through channel, between the coupling sections provided at the two ends, a wall section permeable to an optical sensor signal is formed in a wall of the coupling piece surrounding the flow-through channel, and a receiving housing surrounding the perimeter of the permeable wall section is formed on the coupling piece and comprises a receiving opening positioned opposite the permeable wall section for mounting an optical sensor unit inside of the receiving housing. Thus according to the invention the measurement takes place at the surface of the medium in the flow region of the line system. The measurement area of the sensor and/or its measurement surface is thus a part of the medium channel. Therefore, a separate medium channel which leads to the sensor and which would then lead away from it is unneeded. Furthermore, no opening to the sensor itself is present, so that the urea fluid could penetrate into the sensor itself. According to the invention, the optical sensor emits light preferably in the IR range through the permeable wall section into the medium. In this case the light is reflected from the surface of the urea fluid and is directed back to the sensor by the surface permeable to the sensor signal or by the permeable wall section. The angle of reflection and the intensity of the reflected light are an indication of the quality of the urea fluid. It is advantageous to design the permeable wall section as a breach in the wall. In this case it is an advantage, if the sensor unit comprises a covering on its side opposite the breach, such that the covering closes the open breach and itself consists of a material permeable to the optical sensor signal. By means of this inventive configuration, the sensor unit forms a part of the wall of the flow-through channel. Thus the flow-through channel of the connecting piece is bounded by this covering in the region of the breach. Thus an important manufacturing advantage is attained by the line connector according to the invention, since the line connector can be made in particular of a consistent material as an integral plastics injection molded part. According to the invention, direct contact of the urea fluid with the sensor is prevented.

The advantageous sensor according to the invention is a component part of an enclosed sensor body, so that the sensor located within the sensor body is itself shielded against the present urea fluid. According to the invention, it is an advantage if the sensor body which contains the measurement sensor is sealed by an O-ring gasket from the receiving housing of the line connector. This design of the gasket is distinguished by a simple structure and ensures a sealing to the outside, so that the present urea fluid cannot leak to the outside.

One functional embodiment of an attachment of the sensor body to the receiving housing of the line connector can be implemented, for example, by a material bond, for example, by means of laser welding, wherein this laser welding can be designed as non-circumferential and also not for sealing of the sensor body against the receiving housing. It is used only for holding the sensor body in the receiving housing. As an alternative to the welding of the sensor body to the receiving housing, a mechanical joining between these two parts can be used and specifically, for example, by means of a bayonet-like joint. A clip-like snap-in locking of the two parts would also be advantageous, wherein a detachable and a non-detachable clip joint in the form of a snap-in can be expedient.

It is an advantage that the flow-through channel in the sensor housing comprises an enlarged cross-section compared to the flow-through channels in the adjoining sections, so that a reduction in the speed of the medium flowing in the channels will result.

If the line system in which an invented line connector is integrated, is subjected to repeated empty pumping and refilling, it may be possible that air bubbles will persist in the region of the measurement point and thereby potentially affect the measured result. To solve this problem, it can be expedient according to the invention to provide a constriction of the flow-through channel in the measuring region of the sensor and thus an increase in speed of flow of the medium will occur, which causes any potentially persistent air bubbles to be removed. It is an advantage here that the cross-sectional constriction, proceeding from the particular flow-through channels to the connecting sections, occurs continuously, so that no sudden transition of the different cross sections is present.

Furthermore, according to the invention it can be an advantage that the material sections of the invented line connector surrounding the measurement point, that is for example, the protective caps or the particular opposing contours, are made of a material which is impermeable to UV or IR light, so that these light influences are eliminated, and light permeability is only allowed for the measured wavelength of the optical sensor.

Advantageous designs of the invention are found in the dependent claims. The individual features of the dependent claims can be combined individually or in other combination with the features of the main claim.

According to the invention therefore, a high-precision quality control of the urea fluid is possible directly in the flow-through channel, wherein at temperatures between −8° C. and +80° C., the smallest deviations in the concentration of urea fluid in the range of +/−2% can be detected at concentrations between 20% and 40%, and deviations of +/−3% at concentrations between 10% and 20% and/or 40% to 60%.

According to the invention, the inventive line connector can be integrated into a heated or into a not heated media line, so that an intelligently composed line is created for transmittal of urea fluids, wherein because the line connector can be heated and owing to the connected media line, an accurate and defined operating performance is assured.

BRIEF DESCRIPTION OF THE DRAWINGS

Favorable embodiments of the invention and the invention itself are explained in greater detail below, based on the included figures and illustrated exemplary embodiments. The figures depict.

The same parts in the various figures of the illustrations are always provided with the same reference numbers.

DETAILED DESCRIPTION

With regard to the following specification, the invention is not restricted to the exemplary embodiments and thus not to all or several features of described feature combinations, rather each individual part feature of the/of each exemplary embodiment is also of significance for the subject matter of the invention, even when detached from all other part features described in connection with it, and also in combination with features of any other exemplary embodiment.

Figure 8:
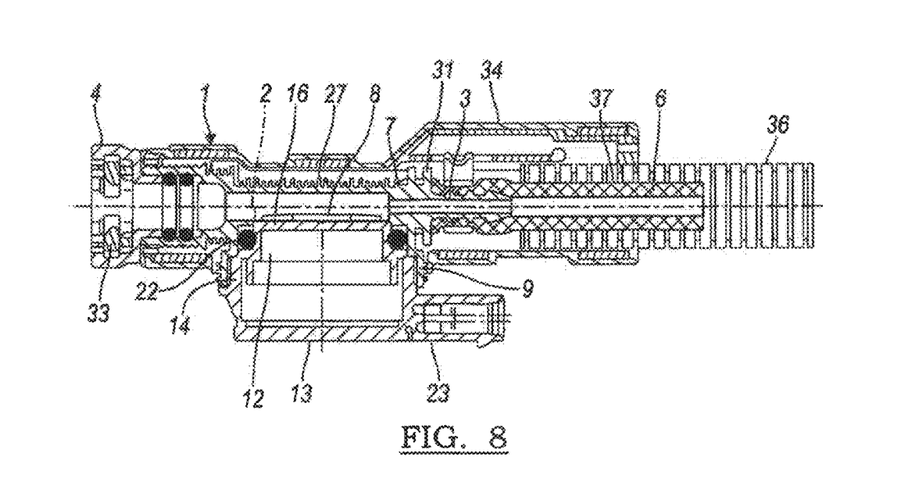
FIG. 8 is a cross section through a line connector according to the invention, with connected media line and external housing.

As is indicated, for example in FIGS. 1 to 6, a line connector according to the invention comprises a connecting piece 1 with a flow-through channel 2 for a fluid, in particular a urea fluid in the interior thereof and extending in the longitudinal direction of the connecting piece 1, wherein the connecting piece 1 comprises at each of its two ends a coupling section 3, 4 which is designed such that a flexible media line 6, see FIG. 8, or a tubing or an aggregate can be connected to an aggregate connector. According to the invention, the flow-through channel 2 is provided with, or can be heated by, an electrical heating unit 7, see FIG. 4.

Figure 5:
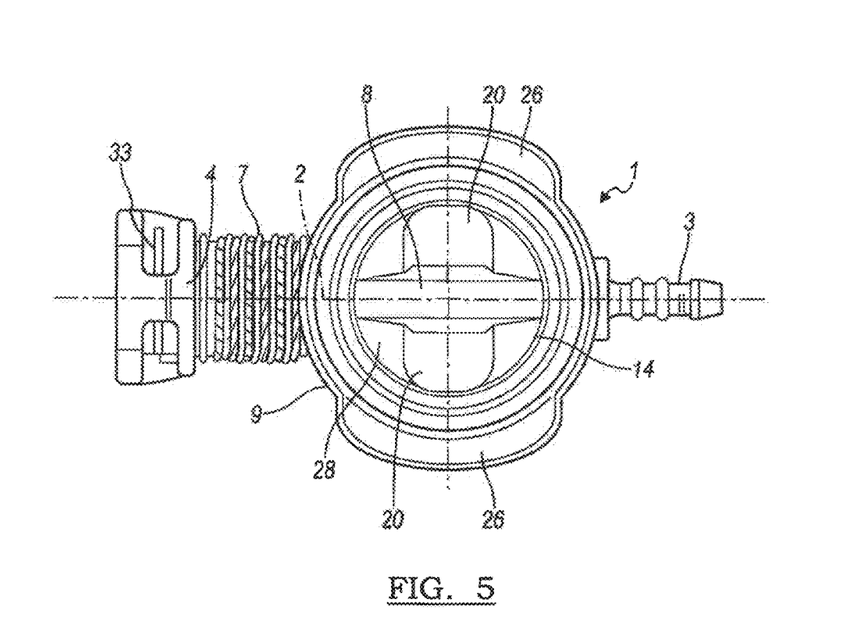
FIG. 5 is a bottom view of the line connector seen in FIG. 1.
Figure 6:
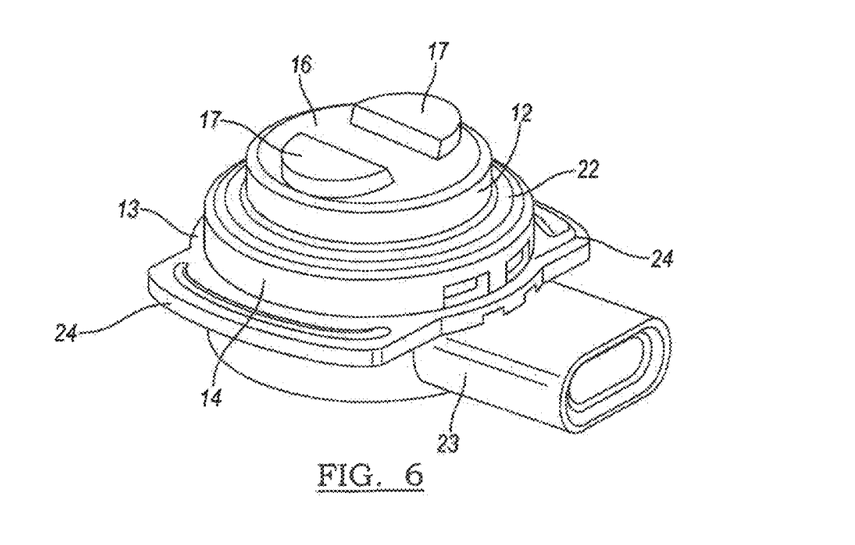
FIG. 6 is a perspective view of a sensor unit according to the invention.

In the region of the flow-through channel 2 between the two coupling sections 3, 4 provided at each of the ends of the flow-through channel 2, there is a wall section permeable to an optical sensor signal located in a wall of the connecting piece 1 surrounding the flow-through channel 2, said wall section 8 is produced as an breach, as is depicted preferably in FIG. 5. A receiving housing 9 surrounds the perimeter of the wall section 8, in particular the breach, which is permeable to an optical sensor signal; the housing is formed on the connecting piece 1. This receiving housing 9 comprises a receiving opening 11 located opposite the wall section 8, through which an optical sensor unit 12 can be installed. An optical sensor unit 12 of this kind is depicted in FIG. 6, for example. An optical sensor unit 12 of this kind is used to measure the quality of the urea fluid flowing in the line connector.

Preferably the connecting piece 1 including the two coupling sections 3, 4 and the receiving housing 9 are designed as a single piece, integral injection molded plastic part. In this case a plastic is used which is suitable for transporting of urea fluids in the SCR method. The optical sensor unit 12 is expediently installed in a closing lid 13 for the receiving opening 11, wherein the closing lid 13 is preferably detachably or non-detachably joined to the receiving housing 9 in its sealed position sealing the receiving opening 11. Preferably the detachable sealed position of the closing lid 13 is produced by means of a bayonet-like connection. The non-detachable sealed position is formed in particular by a material-bonded, or permanently bonded connection, in particular by a laser welded bond. The closing lid 13 comprises preferably an assembly space surrounded by a perimeter wall 14; the optical sensor unit 12 is or can be mounted in this assembly space. The height of the perimeter wall 14 is preferably dimensioned such that the closing lid 13 in its closed position with the perimeter wall 14 passes through the receiving opening 11 into the receiving housing 9.

The assembly space of the closing lid 13 formed by the perimeter wall 14 is preferably equipped with a covering 16 which is optically permeable to optical signals of the optical sensor unit 12. The covering 16 is hereby preferably designed such that it seals the wall section 8 designed as breach in the wall 7 of the flow-through channel 2, so that one wall section of the covering 16 bounds the flow-through channel 2 of the connecting piece 1 and the interior space present in the region of the flow-through channel 2.

As is depicted in FIG. 5 for example, the flow-through channel is disposed between the depressions 20. In this case the flow cross section is expanded in comparison to that of the flow-through channel 2 at the coupling section 3. The flow-through channel 2 for example, comprises a semicircular cross section between the coupling sections 3, 4 and transitions into the depressions 20. In coupling section 4 there is a receiving opening 4a which is dimensioned in particular such that a flow-through channel of a plug-in unit inserted therein comprises an equally sized flow cross section as the flow-through channel of the coupling section 3.

Figure 11:
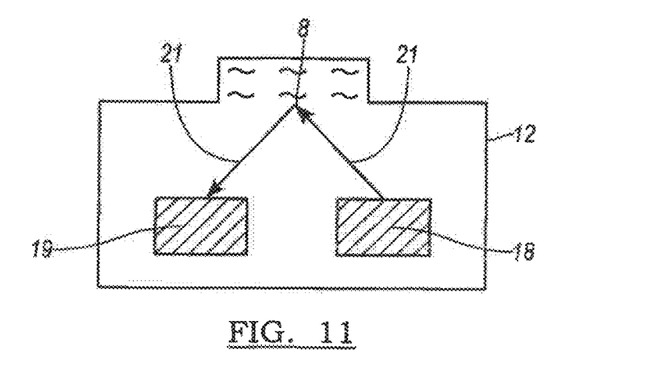
FIG. 11 is a depiction of the measuring principle according to the invention.

Furthermore, it is advantageous if the covering 16 of the closing lid 13 comprises mutually opposing protrusions 17 on both sides of its wall section used to delimit the flow-through channel 2, and each protrusion having a cavity in its interior. An advantageous optical sensor which is arranged within the sensor unit 12, as depicted schematically in FIG. 11, comprises an emitter 18 and an optical receiver 19. The two protrusions 17 serve for mechanical affixing of the optical sensor unit 12. The emitter 18 and the receiver 19 are arranged such that an optical beam path 21, as depicted in FIG. 11, is guided through the wall section 8 to the urea fluid present in the remaining interior space and in particular flowing in the flow-through channel 2, and from there is guided by reflection to the receiver 19, if the sensor unit 12 is completely installed in the receiving housing 9.

Furthermore, it is advantageous to provide a depression 20 in one bottom section 28 of the receiving housing 9 on both sides of the permeable wall section 8, especially of the breach, to accommodate one of the protrusions 17 of the optical sensor unit 12. Thus both a secure covering of the wall section 8 designed, for example as a breach, and also an unhindered irradiation of the optical signal 21 onto the fluid present in the region of the flow-through channel 2 is assured.

As is illustrated in particular in FIG. 6, a recess is formed at the free end of the perimeter wall 14, for example, on which a perimeter gasket 22 is seated and which is designed preferably as an elastically deformable O-ring gasket.

The perimeter gasket 22 ensures a fluid-tight sealing between the closing lid 13 and the receiving housing 9 in the closed position of the lid 13. A coupling portion 23 is formed on the optical sensor unit 12 which is used for connection of an electrical power supply to the sensor arranged within the sensor unit 12.

At the outer perimeter of its perimeter wall 14, the sensor unit 12 comprises preferably web-like extensions 24 directed perpendicular to said perimeter wall; the protrusions have preferably an arc-like shape and are positioned diametrically opposite each other, see FIG. 6. Preferably the receiving housing 9 in the plugged-in state of the sensor unit 12 has arc-like, web-shaped extensions 26 positioned opposite the web-shaped extensions 24 of the sensor unit 12, see FIG. 5. In the region of these web-shaped extensions 24, 26 of the sensor unit 12 and of the receiving housing 9, the sensor unit 12 in the assembled state can be bonded to the receiving housing 9, as already explained, either by a material bond or interlocking bond.

Figure 1:
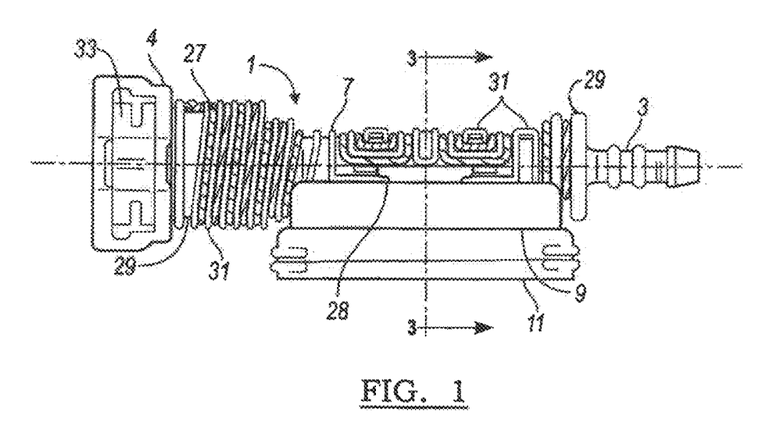
FIG. 1 is a side view of a line connector according to the invention.
Figure 2:
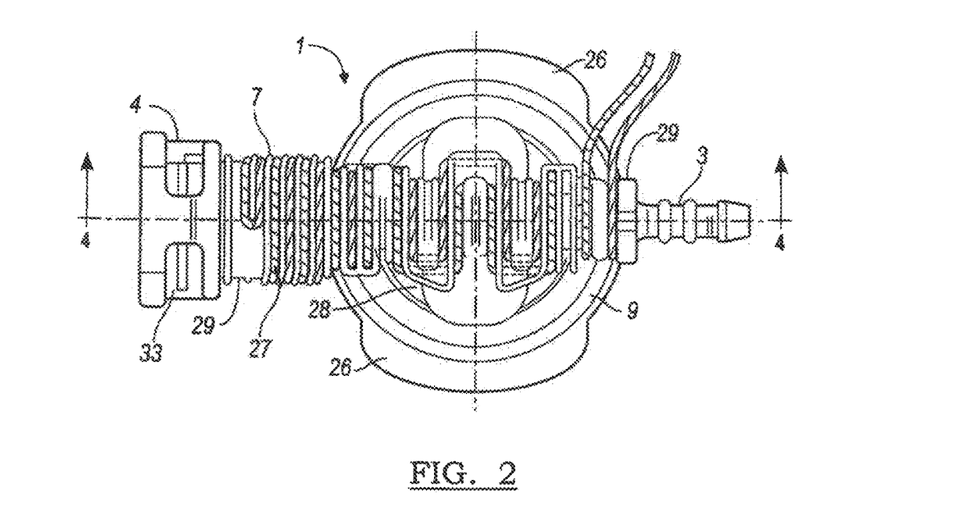
FIG. 2 is a top view of the line connector seen in FIG. 1.
Figure 3:
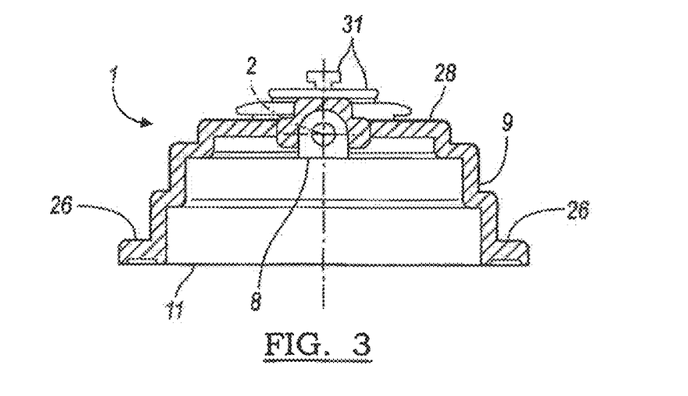
FIG. 3 is a cross-section along cut line 3-3 in FIG. 1.
Figure 4:
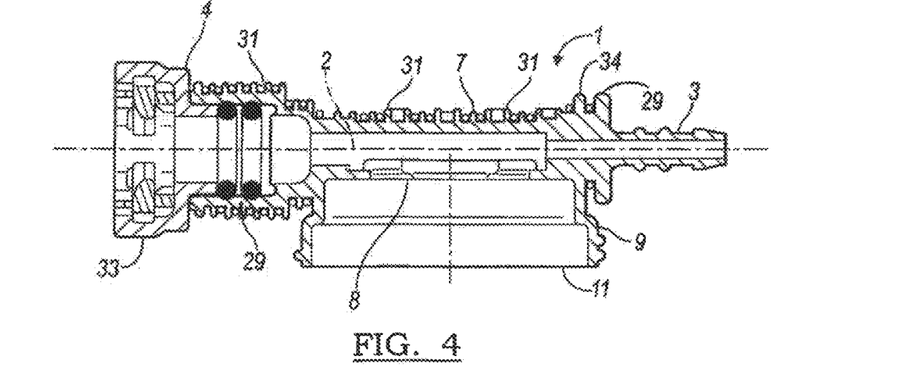
FIG. 4 is a longitudinal cross-section along cut line 4-4 in FIG. 2.

As is illustrated especially in FIGS. 1, 2 and 4, an electric heating unit 7 composed from the heating elements located there is disposed at the outside of the connecting piece 1 and serves for heating of the fluid flowing in the connecting piece 1, that is heating of the urea fluid. In the depicted exemplary embodiment, the heating elements are composed of an electrically conducting wire 27. This conducting wire 27 extends in the region between the coupling sections 3, 4 on the outside of the connecting piece 1, in particular on the outside of the receiving housing 9, and specifically on the outside of the bottom section 28 of the receiving housing 9. Preferably the conductor wire 27 extends in a meander-like formation parallel to the bottom section 28; and in the region of the cylindrical sections 29 of the connecting piece 1 located between the bottom section 28 and the coupling sections 3, 4, the conductor wire 27 extends in a spiral shape winding around the perimeter of the cylindrical shaped sections 29. The free ends of the conductor wire 27 are guided in particular such that they can be connected electrically to external electrical power supply wires, for example, by clamping means. Likewise it is within the scope of the invention that the conductor wire 27 located on the connecting piece 1 is an extension of an electrical heating conductor 37, which is connected to a media line 6 joined to the line connector and/or to the connecting piece 1. The conductor wire 27 located on the connecting piece 1 can be circuited in series or in parallel with the electrical heating conductor 37 disposed on a connected media line 6, and specifically by means of a corresponding electric clamp connection or solder connection.

In addition, it can be an advantage according to the invention, when the electrical conductor wire 27 which is disposed on the connecting piece 1, is guided and secured along its progression on the connecting piece 1 by means of guide elements 31 which are designed as web-shaped or rib-shaped or even as guide grooves. This guiding and securing of the conductor wire 27 can also be provided only on sections.

Figure 7:
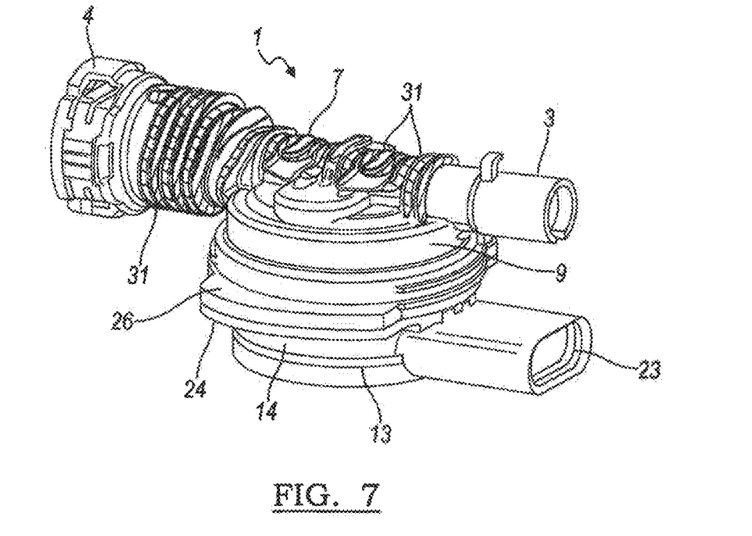
FIG. 7 is a perspective view of an additional embodiment of a line connector with attached sensor unit according to the invention.

FIG. 1 illustrates that one of the coupling sections, and specifically the coupling section 3 in the illustrated exemplary embodiment, is shaped as a coupling mandrel onto which a flexible media line 6 is plugged, as is evident in FIG. 8. FIG. 7 depicts an alternative embodiment, and here the coupling section 3 is designed as a sleeve-like receiving element into which a media line 6, in particular a tube, can be inserted, and a firmly bonded connection is established between the inserted tube and the sleeve-like receiving element, for example, by means of laser welding.

Figure 10:
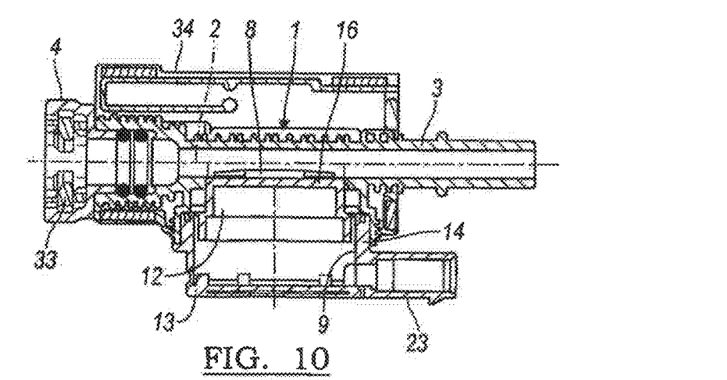
FIG. 10 is a longitudinal cross section through an additional design of a line connector according to the invention.

FIG. 10 illustrates an embodiment in which the coupling section 3 is designed as an SAE-coupler in the form of a tubular coupling piece onto which a media line 6 is plugged, and is secured for example with a clamp.

The coupling section 4 in the illustrated exemplary embodiments is represented as a sleeve section with release elements 33 formed thereon, so that an insertion element, for example a plug, can be inserted into and locked in this sleeve section, and thus secured by means of the release elements 33. In order to extract this insertion element again, the release elements 33 are actuated, for example, by spreading, and the insertion element can be withdrawn from the sleeve section.

Figure 9:
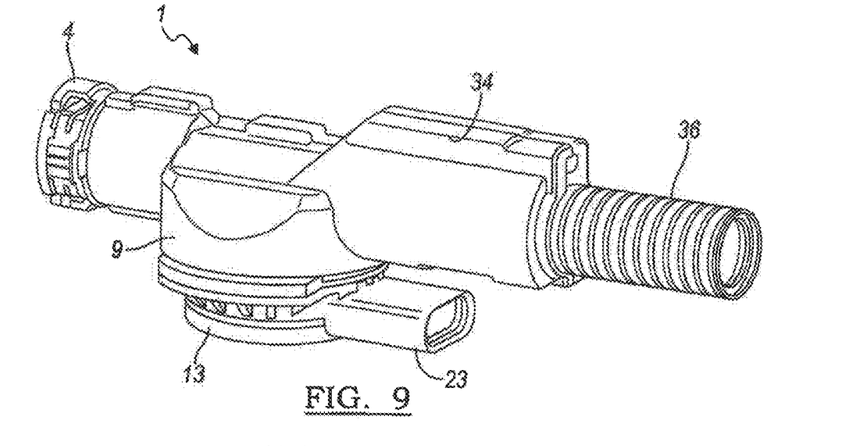
FIG. 9 is a perspective view of the line connector according to FIG. 8.

As is indicated in particular in FIGS. 8 and 9, it can be advantageous according to the invention, when the connecting piece 1 is surrounded by an encapsulation 34, especially of plastic, proceeding from the region between the coupling section 4 equipped with release elements 33, out to beyond the region or up to the opposing coupling section 3, and extending past this coupling section in the longitudinal direction. This kind of encapsulation, prevents any mechanical influence of the connecting piece 1 and of the heating elements 7 located thereon, and in addition, the radiation of heat to the outside is reduced. Furthermore, this housing can be designed such that it comprises a chamber to accommodate an electrical connector between the ends of the heating elements 7 located on the connecting piece 1 and the ends of electrical connectors introduced from the outside, and also any media line connected to ends of heating conductors. In one advantageous embodiment, this kind of encapsulation 34 can be formed from two housing halves so that a housing is produced, wherein the housing halves are joined together, in particular in a detachable manner, by means of snap-in fittings.

Figure 12:
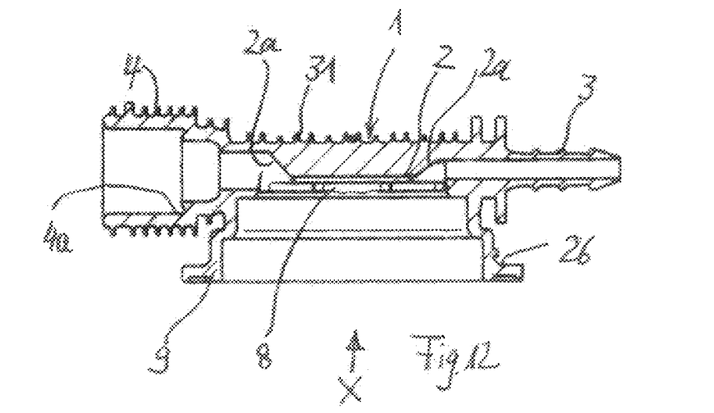
FIG. 12 is a longitudinal cross section through an additional design of a line connector according to the invention.
Figure 13:
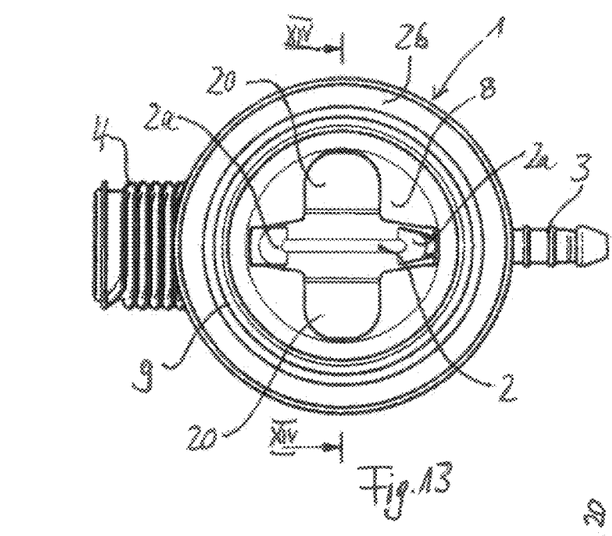
FIG. 13 is a bottom view of the line connector generally in the direction of arrow X in FIG. 12.
Figure 14:
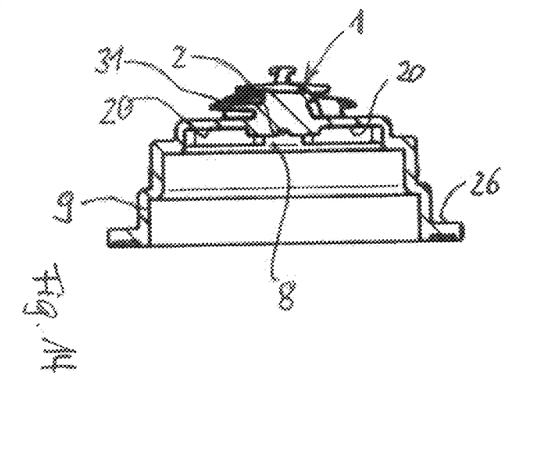
FIG. 14 is a cross section through a line connector according to the FIG. 13 along the cut line XIV-XIV.

FIG. 12 depicts an alternative design of the flow-through channel 2. In this case the flow cross section of the flow-through channel 2 is reduced in comparison to the flow cross section of the flow-through channel in the coupling section 3. This also applies in respect to the flow-through channel of an insertion unit inserted into the receiving opening 4a of the coupling section 4. Thus an increase in speed is obtained in the region of the flow-through channel 2 of the flowing medium, and in particular in the region of the measurement point, and specifically in comparison to the flow speed in the flow-through channel of the coupling section 3 and in the flow-through channel of the insertion unit inserted into the receiving opening 4a. Due to this design, the problem of air occlusions present in the medium, e.g. a urea fluid, flowing in the flow-through channel, are prevented from persisting or collecting in the region of the measurement point. Due to the invented reduction in the flow cross section in the region of the flow-through channel and/or the measurement point, the flow speed of the flowing medium is increased and this ensures that any present air bubbles will no longer collect in the region of the measurement point, but rather are thereby flushed away. Thus the measurement accuracy can no longer be affected by this kind of air bubbles.

It is expedient that the total cross section of the flow section beneath the sensor measuring point—which is formed from the flow cross section of the flow-through channel 2 and the adjoining region likewise with flowing medium—amounts to 60% to 75% of the flow cross section (inlet cross section) in the coupling section 3. With regard to the flow cross section of the flow-through channel 2, it is expedient that it amounts to ⅓ of the flow cross section in the coupling section 3, for example. If the diameter of the flow channel in the coupling section 3 amounts to 6 mm, for example, then the diameter of the flow-through channel beneath the sensor measurement point amounts to 2 mm, for example.

As is evident in the figures, the reduction in the flow cross section of the flow-through channel 2 is achieved expediently by an enlargement of the wall thickness of the wall between the coupling sections 3, 4. Preferably the transition between the flow-through channel in the coupling section 3 and that in coupling section 4 progresses continuously, for example, by means of slanting surfaces 2a.

The expedient embodiment of the flow-through channel described above is based on the fundamental teaching according to the invention, that at measurement points where the characteristics of the flowing media are measured by means of sensors, in particular optical sensors, the flow speed is increased expediently—and specifically compared to the flow speed of the medium to be measured in front of and behind the particular measurement point—such that air bubbles or other particles affecting the measurement cannot collect in the region of the measurement point. It is expedient in particular not to provide a sudden transition between the different flow cross sections, but rather a continuous transition between the flow cross sections, so that thus a smoothing of the flow is effected. It is expedient herein to use a design like a Venturi valve, for example.

Due to the reduction in the flow cross section in the region of the measurement point, the additional effect is that due to the resultant reduction in the liquid volume in case of freezing of the flow liquid, any resulting ice pressure is likewise reduced, so that the danger of damage to the measurement sensor or a destruction of the measurement apparatus can be essentially minimized.

Furthermore it can be expedient according to the invention, due to a corresponding configuration of the flow-through channel in front of and/or behind the measurement point, that gas and/or air bubbles contained in the flow medium collect directly next to and/or above and/or under the measurement point. Gas bubbles and/or air bubbles of this kind do not disrupt the measurement, and in the event of freezing of the flow medium, ice volumes can collect in this region and thus the resulting ice pressure can be reduced.

Furthermore, it can be expedient to eliminate the influence of ambient light on the measurement of the characteristics of a medium, in particular of a liquid medium, for example an SCR fluid by means of an optical sensor, at a measurement point. For this purpose, the material—especially plastic—surrounding the measurement sensors in the region of the measurement point, meaning for example the existing counter-contour to the measuring apparatus or existing coverings, is designed such that it is impermeable to the wavelength of the ambient light, in particular to any present UV and/or IR radiation. This produces a filter for the measurement wavelength of the optical sensor, wherein the material is only transmissive for this wavelength. When using laser light for the measurement, the material surrounding the measurement sensor would be transparent to laser radiation.

As is illustrated in FIG. 8, a line connector according to the invention can be a component part of a ready-made media line, so that the connecting piece 1 is connected, for example, in the region of its coupling section 3 to a media line 6 secured thereon. This media line 6 can be surrounded by an outer, tubular sheathing 36, wherein this can be in particular a corrugated tube. Preferably this tube is inserted by one end into the housing 34 and can be form fitted to the housing 34.

FIG. 10 depicts a so-called "stand-alone" variant of a line connector according to the invention. In this case the housing 34 extends between the exposed coupling section 4 and the transition of the coupling section 3 to the cylindrical-shaped section 29, so that the coupling section 3 is exposed, and is designed, for example, as an SAE coupling. The housing 34 comprises a chamber extending across the length of the heated region to accommodate the electrical connector wire and the electrical connections between the connector wires and the electrical conductors for heating of the connecting plug.

It remains within the scope of the invention to design the line connector according to the invention with coupling sections 3 on both sides, as described above. Also, the line connector according to the invention can be designed as an angled line connector.

The invention is not restricted to the illustrated and described exemplary embodiments, but rather encompasses also all equivalent designs within the sense of the invention. It is expressly emphasized that the exemplary embodiments are not restricted to all features in combination, rather each individual part feature can have inventive significance independently and detached from all other part features. Furthermore, the invention is not restricted to the combination of features defined in claim 1, but rather can also be defined by any other particular combination of specific features of all the disclosed individual features. This means that basically practically every individual feature of claim 1 can be omitted, and/or can be replaced by at least one other individual feature disclosed elsewhere in the application.

The invention claimed is:

1. A line connector for a fluid, the line connector comprising a connecting piece with a flow-through channel configured to contact flowing fluid in an interior thereof and extending in a longitudinal direction of the connecting piece, the connecting piece having a coupling section at each end thereof configured to connect a flexible media line or a tubing or an aggregate to an aggregate connector, the flow-through channel being provided with an electrical heating unit, an optically permeable wall section being formed in a wall of the coupling piece surrounding the flow-through channel and between the coupling sections, and a receiving housing closed about its circumference being formed on the connecting piece and surrounding the permeable wall section, the receiving housing including a receiving opening positioned opposite the permeable wall section and configured for mounting of an optical sensor unit inside of the receiving housing, a flow cross-section of the flow-through channel defined adjacent to the permeable wall section being smaller than an effective flow cross-section of the flow-through channel defined in the coupling sections.

2. The line connector according to claim 1, wherein the connecting piece together with the receiving housing is as a single piece, plastic molded part.

3. The line connector according to claim 1, wherein the connecting piece is formed of a plastic material impervious to urea fluids used with SCR-catalysts.

4. The line connector according to claim 1, wherein the permeable wall section is an open breach.

5. The line connector according to claim 1, further comprising a closing lid moveable to a closed position closing off the receiving opening, the closing lip being one of detachably or non-detachably connected to the receiving housing.

6. The line connector according to claim 5, wherein the detachable connection of the closing lid is formed by a bayonet connector.

7. The line connector according to claim 5, wherein the non-detachable connection of the closing lid is formed by a laser welded bonded connection.

8. The line connector according to claim 5, wherein the closing lid includes an assembly space surrounded by a perimeter wall, the assembly space in the closed position extending through the receiving opening of the receiving housing, wherein the optical sensor unit is mounted in the receiving space.

9. The line connector according to claim 5, further comprising a perimeter gasket arranged between the closing lid in its closed position and the receiving housing and forming a fluid tight seal therebetween.

10. The line connector according to claim 8, wherein the assembly space of the closing lid is closed off at a side facing an open breach of the permeable wall section by a covering permeable to optical signals of the optical sensor unit, the optical sensor unit being enclosed by the covering in the assembly space, the covering sealing the open breach such that one wall section of the covering borders the flow-through channel of the connecting piece.

11. The line connector according to claim 10, wherein on both sides of the one wall section the covering includes mutually opposing protrusions mechanically affixed to the optical sensor unit, an emitter and a receiver of the optical sensor unit being arranged such that an optical beam path is guided from the emitter via the breach to the medium present in the region of the flow-through channel, and from there, by reflection to the receiver.

12. The line connector according to claim 11, wherein a recess is defined in a bottom section of the receiving housing on both sides of the open breach, each recess accommodating one of the protrusions.

13. The line connector according to claim 1, wherein a continuous transition is provided between the flow cross-sections of the flow-through channel defined adjacent to the permeable wall section and defined in the coupling sections.

14. The line connector according to claim 1, wherein an electrical power supply coupling portion is formed on the optical sensor unit in the region of the closing lid.

15. The line connector according to claim 1, wherein the electrical heating unit is formed from heating elements disposed along the outside of the connecting piece.

16. The line connector according to claim 15, wherein the heating unit is formed from at least one electrical conductor wire meandering in the region of the connecting piece between the coupling sections on an outside of a bottom section of the receiving housing, on the outside of the wall of the flow-through channel, and in a region of cylindrical sections of the connecting piece, the conductor wire proceeding spiral-like between the bottom section and the coupling sections, and two ends of the conductor wire being designed and disposed for coupling to separate electrical supply lines.

17. The line connector according to claim 16, wherein the electrical conductor wire is at least partially guided by guide elements over its entire progression to the connecting piece.

18. The line connector according to claim 16, wherein the coupling sections are designed as one of sleeve sections with detachment elements arranged thereon for detachable inserting of insertion elements, coupling elements for pushing on of a media line to be connected, sleeve-like receiving elements for snap-in receiving of a media line to be connected and for material bonding connection therewith.

19. The line connector according to claim 1 wherein one of the coupling sections is equipped with release elements, the connecting piece being surrounded by an encapsulation between the coupling section equipped with release elements and beyond a region or up to a region of the other coupling section.

20. The line connector according to claim 19, wherein the encapsulation is combined into one housing from two housing shells that are detachably joined together by snap-in elements.

21. The line connector according to claim 19, wherein one of the encapsulation or the housing comprises a receiving chamber for receiving electrical connecting elements for connecting the ends of the conductor wire to electrical coupling wires of an external power supply or for connecting ends of a heating conductor of a media line connected thereto.

22. A ready-made media line, comprising a line connector according to claim 1 connected on at least one side to a tubular media line.

23. The ready-made media line according to claim 22, wherein the tubular media line is surrounded by a mantle tube, and the media line is spiral wrapped by a heating conductor in a longitudinal direction, wherein the mantle tube is introduced into one of an encapsulation and the housing by an end of the mantle tube inserted into the encapsulation or the housing, and the mantle tube being connected in a form fitted manner to one of the encapsulation or the housing, and the heating wire of the media line being one of electrically connected to an external power supply via a connecting line or to the conductor wire of the connecting piece by one of a series or parallel circuit.

\* \* \* \* \*